(12) United States Patent
Arthur et al.

(10) Patent No.: US 9,820,807 B2
(45) Date of Patent: Nov. 21, 2017

(54) BLUNT TIP SURGICAL CUTTING DEVICE AND METHOD

(71) Applicant: KYPHON SARL, Neuchatel (CH)

(72) Inventors: Amy L. Arthur, Mountain View, CA (US); Calin Druma, San Jose, CA (US); Michael A. Smith, San Jose, CA (US)

(73) Assignee: Kyphon SÀRL, Neuchâtel (CH)

( * ) Notice: Subject to any disclaimer, the term of this patent is extended or adjusted under 35 U.S.C. 154(b) by 0 days.

(21) Appl. No.: 15/238,347

(22) Filed: Aug. 16, 2016

(65) Prior Publication Data

US 2017/0035495 A1 Feb. 9, 2017

Related U.S. Application Data

(62) Division of application No. 13/830,352, filed on Mar. 14, 2013, now Pat. No. 9,414,858.

(51) Int. Cl.

| *A61B 18/14* | (2006.01) |
|---|---|
| *A61B 17/34* | (2006.01) |
| *A61B 18/04* | (2006.01) |
| *A61B 18/12* | (2006.01) |
| A61B 18/00 | (2006.01) |
| A61B 17/00 | (2006.01) |

(52) U.S. Cl.
CPC ...... *A61B 18/1477* (2013.01); *A61B 17/3496* (2013.01); *A61B 18/042* (2013.01); *A61B 18/12* (2013.01); *A61B 2017/0073* (2013.01); *A61B 2018/00601* (2013.01); *A61B 2018/1425* (2013.01); *A61B 2018/1475* (2013.01)

(58) Field of Classification Search
CPC ........ A61B 17/3496; A61B 2018/1475; A61B 18/1477
See application file for complete search history.

(56) References Cited

U.S. PATENT DOCUMENTS

| 5,769,826 A | 6/1998 | Johnson et al. |
|---|---|---|
| 5,989,220 A | 11/1999 | Shaw et al. |
| 6,162,197 A | 12/2000 | Mohammad |
| 6,273,861 B1 | 8/2001 | Bates et al. |
| 8,066,718 B2 | 11/2011 | Weisel et al. |
| 8,357,103 B2 | 1/2013 | Mark et al. |
| 2009/0036958 A1 | 2/2009 | Mehta |
| 2011/0270239 A1 | 11/2011 | Werneth |
| 2012/0116397 A1 | 5/2012 | Rencher et al. |

*Primary Examiner* — Michael Kahelin

(57) ABSTRACT

A cutting device includes an elongated shaft extending between a proximal end and a distal end. A lower portion extends from the distal end of the elongated shaft and includes an outer surface and an inner surface spaced apart from the outer surface which together form a blunt end configured as a stop so as to protect adjacent tissue. An upper portion extends from the distal end of the elongated shaft and including an inner surface. The upper portion is configured so as to be disposed opposite the lower portion. A cutting element is disposed between the lower portion and the upper portion and is configured for retractable extension beyond the distal end of the elongated shaft so as to contact tissue.

20 Claims, 2 Drawing Sheets

BLUNT TIP SURGICAL CUTTING DEVICE AND METHOD

This application is a divisional of application Ser. No. 13/830,352 (now U.S. Pat. No. 9,414,858), filed Mar. 14, 2013, all of which is incorporated herein by reference.

FIELD OF THE INVENTION

The present invention relates generally to devices and methods for cutting a material or substance. More specifically, the devices and methods are useful for resecting nerve and/or soft tissue via a minimally invasive procedure to alleviate pain.

BACKGROUND OF THE INVENTION

Standard methods of cutting tissue may include using a scalpel, scissors, and radio frequency energy. Electrosurgical procedures and techniques using radio frequency energy are currently used since they generally reduce patient bleeding and trauma associated with cutting operations. Additionally, electrosurgical ablation procedures, where tissue surfaces and volume may be reshaped, cannot be duplicated through other treatment modalities.

Minimally invasive procedures in nerve and/or soft tissue such as the spine or the breast, however, are difficult to perform using standard scissors and scalpel. Furthermore, in a closed environment, radio frequency current dissipates into the surrounding tissue causing a decreased ability to achieve a current at the cutting electrode of sufficiently high density to initiate a cut. To overcome this problem, high power settings are often required to initiate the cut which often is painful and increases thermal damage to the tissue whether using a standard or a custom electrosurgical generator.

Another problem associated with cutting tissue is the control of bleeding. Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

A further disadvantage of using radio frequency energy is the generation of smoke. The smoke is malodorous and can contain airborne viral particles that may be infectious. Furthermore, the smoke often obscures visualization of the procedure. When the smoke becomes too dense, the procedure is delayed until the smoke is released through one of the trocar ports and after enough carbon dioxide gas has re-insufflated the abdominal cavity. This unnecessarily prolongs the operative time.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices are wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures.

Traditional monopolar RF systems can provide fine dissection capabilities of soft tissue, but may also cause a high level of collateral thermal damage. Further, these devices may suffer from an inability to control the depth of necrosis in the tissue being treated. The high heat intensity generated by these systems causes burning and charring of the surrounding tissue, leading to increased pain and slower recovery of the remaining tissue. Further, the desire for an electrosurgical device to provide for fine dissection of soft tissue may compromise the ability to provide consistent ablative cutting without significant collateral damage while allowing for concomitant hemostasis and good coagulation of the remaining tissue.

Another problem with currently available RF nerve ablation devices is that they attempt to destroy nerve tissue from a central location including the tip of the device and a 3-D spherical or cylindrical zone around it. As a result, the further away the resecting ability is from the central zone the less effective the nerve destruction. Consequently, often the nerve is not adequately ablated leading to continued pain symptoms.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Other devices such as mechanical rongeurs can be used to remove soft tissue. However, these devices require the insertion of relatively large cannulas that further complicate the surgical procedure and can cause nerve compression and pain with variable clinical efficacy.

Accordingly, there is a need for devices and methods to provide efficient severing or cutting of nerve and/or soft tissue that can be used during a minimally invasive procedure and/or during an open surgical procedure. Further, there is also a need for devices and methods that provide fine dissection capabilities of nerve and/or soft tissue. Devices and methods that do not cause a high level of collateral thermal damage and allow for the control of necrosis in the tissue being treated are also needed. Devices and methods that provide efficient, controlled and safe debulking of tissue would also be beneficial.

SUMMARY OF THE INVENTION

In accordance with the principles of this disclosure, a cutting device is disclosed, which includes an elongated shaft extending between a proximal end and a distal end. A lower portion extends from the distal end of the elongated shaft and includes an outer surface and an inner surface spaced apart from the outer surface which together form a blunt end configured as a stop so as to protect adjacent tissue. An upper portion extends from the distal end of the elongated shaft and includes an inner surface. The upper portion is configured so as to be disposed opposite the lower portion. A cutting element is disposed between the lower portion and the upper portion and is configured for retractable extension beyond the distal end of the elongated shaft so as to contact tissue.

In one embodiment, a cutting device for cutting tissue comprises an elongated shaft extending between a proximal end and a distal end. A lower portion extends from the distal end of the elongated shaft and includes an outer surface and an inner surface spaced apart from the outer surface which together form a blunt end configured as a stop so as to protect adjacent tissue. An upper portion extends from the distal end of the elongated shaft and includes an inner surface. The upper portion is configured so as to be disposed opposite the lower portion. A cutting element is resiliently biased between the lower portion and the upper portion and is configured for retractable extension beyond the distal end of the elongated shaft so as to contact tissue. An attachment to a vacuum is disposed at the proximal end of the elongated shaft to produce suction to facilitate removal of tissue from the cavity.

In one embodiment, a method of cutting tissue is disclosed. A cannula is inserted into the anatomy of a patient to form a hole in the tissue. A cutting device is inserted through the cannula. The blunt tip is slid along a lamina of a patient to prevent damage to tissue. A spring loaded cutting tip is compressed to extend the cutting tip beyond the upper and lower arms to cut tissue. The cutting tip is retracted back into the cavity. The cutting device and the cannula are then removed from the patient.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Like reference numerals indicate similar parts throughout the figures.

DETAILED DESCRIPTION OF THE INVENTION

Figure 1:
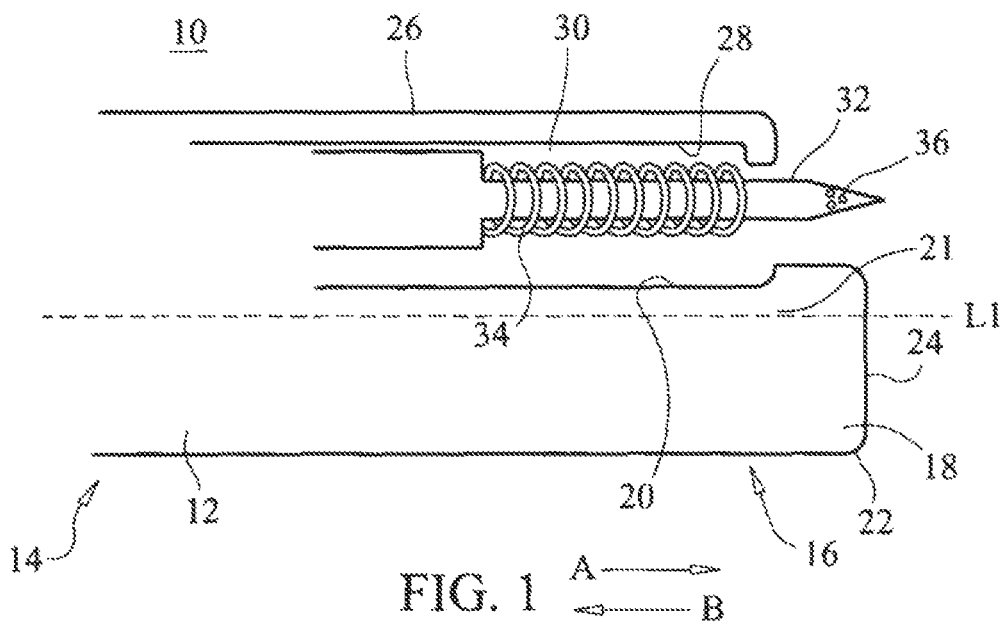
FIG. 1 is a side cross sectional view of an embodiment of the device in accordance with the principles of the present disclosure.

Devices for efficient severing or cutting of a material or substance such as nerve and/or soft tissue suitable for use in open surgical and/or minimally invasive procedures are disclosed. The following description is presented to enable any person skilled in the art to make and use the present disclosure. Descriptions of specific embodiments and applications are provided only as examples and various modifications will be readily apparent to those skilled in the art.

Lumbar spinal stenosis (LSS) may occur from hypertrophied bone or ligamentum flavum, or from a lax ligamentum flavum that collapses into the spinal canal. LSS can present clinical symptoms such as leg pain and reduced function. Conventional treatments include epidural steroid injections, laminotomy, and laminectomy. Surgical interventions which remove at least some portion of the lamina are usually performed through a relatively large incision, and may result in spinal instability from removal of a large portion of the lamina. Consequently, a more percutaneous approach which removes just enough tissue (lamina or ligamentum flavum) to be effective may be more beneficial.

In one embodiment, the device includes a cutting tip positioned on a distal end of a spring loaded tool. As the spring is compressed, the cutting tip extends beyond distal end of tool to contact and cut tissue. As the spring is released, the cutting tip retracts into the tool such that it does not contact tissue. A blunt distal end of the tool contacts bone to act as stop. The blunt surface is configured to ride along the lamina and may deliver RF energy to the tissue to be cut.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof)

means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

For purposes of the description contained herein, "vacuum" means pressure within a space that is lower by any amount than atmospheric or ambient pressure, and although not exclusive of a condition of absolute vacuum defined by a complete absence within a space of air, fluid or other matter, the term as used herein is not meant to require or be limited to such a condition.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Radiofrequency (RF) ablation devices have been available to surgeons to treat many medical conditions, for example, in the treatment of tumors in lung, liver, kidney, bone and other body organs. Pulsed RF has also been used for treatment of tumors, cardiac arrhythmias, chronic and post-operative pain, bone fracture and soft tissue wounds.

The components of the cutting device can be fabricated from biologically acceptable materials suitable for medical apparatuses, including metals, synthetic polymers, ceramics, thermoplastic and polymeric material and/or their composites. For example, the components of the holding device, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, and composites of metals and calcium-based ceramics, composites of PEEK and calcium based ceramics, and combinations of the above materials.

Various components of the holding device may have material composites, including the above materials, to achieve various desired characteristics such as strength, rigidity, elasticity, compliance, and biomechanical performance, durability and to provide a non-stick surface. The components of the holding device may be monolithically formed, extruded, coextruded, hot molded, cold molded, press molded, integrally connected or include fastening elements and/or coupling components, as described herein.

Figure 2:
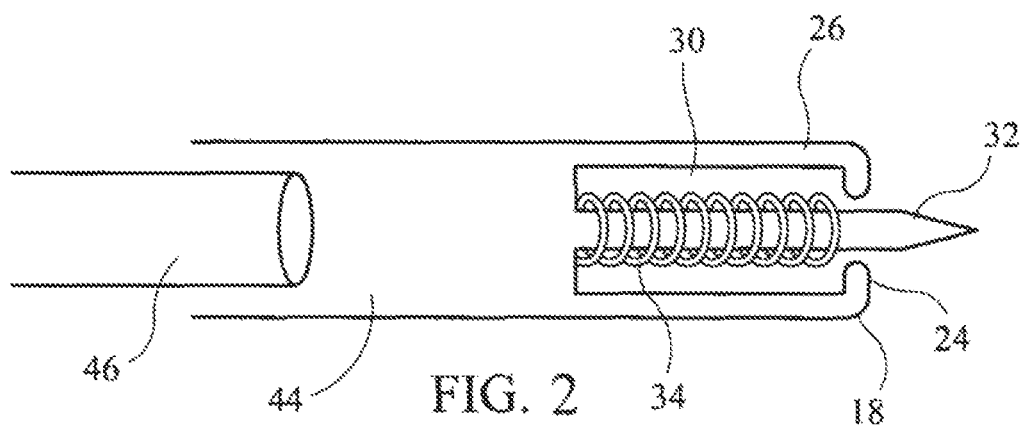
FIG. 2 is side cross sectional view of an embodiment of the device in accordance with the principles of the present disclosure.

In one embodiment, as shown in FIGS. 1-2, the cutting device 10, in accordance with the present disclosure, includes an elongated shaft 12. Shaft 12 extends between a proximal end 14 and a distal end 16 and defines a longitudinal axis L1. It is envisioned that all or only a portion of shaft 12 may have various cross section configurations, such as, for example, cylindrical, flat, oval, oblong, triangular, square, polygonal, irregular, uniform, non-uniform, offset, staggered, undulating, arcuate, variable and/or tapered. In various embodiments, the navigational sources can be coupled with a pre-procedure such as for example, CT, MRI, PET scan, etc. so that the target nerve or soft tissue to be cut can be identified and accurately located during the procedure.

A lower portion 18 extends from distal end 16 of shaft 12. Portion 18 includes an inner surface 20 and an outer surface 22 spaced apart from the inner surface 20. Surfaces 20, 22 together forms a blunt end 24 configured as a stop to protect adjacent tissue. It is contemplated that surfaces 20 and 22 include various surface configurations, such as, for example, smooth, rough, mesh, porous, semi-porous, dimpled and/or textured.

An upper portion 26 extends from distal end 16 of shaft 12 and is disposed opposite portion 18. Portion 26 includes an inner surface 28. It is contemplated that surface 28 includes various surface configurations, such as, for example, smooth, rough, mesh, porous, semi-porous, dimpled and/or textured. Surface 20 and surface 28 are configured to form a cavity 30. Cavity 30 is configured to house a cutting element 32, discussed below. In some embodiments, cavity 30 can have a cross section being cylindrical, flat, oval, oblong, triangular, square, polygonal, irregular, uniform, non-uniform, offset, staggered, undulating, arcuate, variable and/or tapered.

Device 10 includes a cutting element 32. Cutting element 32 is configured to contact and/or cut tissue. Cutting element 32 is resiliently biased, such as, for example, with a spring 34 within cavity 30 such that cutting element 32 extends out of cavity 30 to contact and/or cut tissue. In some embodiments, the resiliently biased member can include a semi-rigid, rigid or elastic configuration, and/or have elastic properties, such as the elastic properties corresponding to the material examples described above, such that the resiliently biasing member provides a selective amount of expansion, contraction, collapse and/or extension.

In one embodiment, cutting element 32 includes electrodes 36 configured to emit a RF frequency adapted for cutting nerve and/or soft tissue. In one embodiment, cutting element 32 is configured to emit pulsed plasma signals adapted for cutting nerve and/or soft tissue. In one embodiment, device 10 includes an electrically insulated layer adjacent to and exposing cutting element 32 such that the energy transmitted from the RF frequency and/or the plasma is centralized at cutting element 32. In some embodiments, the coating or insulating layer can be glass or ceramic having a thickness from about 0.005 to about 0.5 mm thick or from about 0.01 to about 0.2 mm thick. By moving cutting element 32 across tissue, the RF or plasma signals will cut the tissue.

In one embodiment, shaft 12 includes an internal passage 44 configured to engage a vacuum 46, as shown in FIG. 2, to suction the resected nerve and/or soft tissue. Alternatively, an additional channel is possible for delivering fluid to the surgical site. At its proximate end, shaft 12 can be operatively connected to vacuum 46 for providing suction to resected nerve and/or tissue. Vacuum 46 may be used to transmit vacuum from a vacuum source (not shown) to a receiving aperture connected to shaft 12. Any suitable aspirator, cylindrical or otherwise, or other mechanism that creates vacuum upon the movement of an actuating member thereof, may be utilized as a vacuum source. Vacuum 46 can be in fluid communication with cavity 24 for providing suction to remove cut nerve and/or soft tissue.

The present disclosure also provides methods for cutting or resectioning nerve and/or soft tissue. The methods comprise positioning a distal region of shaft 12 of cutting device 10 adjacent a nerve or soft tissue to be cut. End 24 is blunt so as not to pierce certain areas of the patient, such as, for example, the spinal cord. In addition, the blunt surface is configured to ride or follow along a relatively rigid structure, such as the lamina, and the cutting element advances to a tissue distal to the rigid structure, such as the ligamentum flavum. Distal end 16 is positioned at the area where the tissue is to be cut. To cut the tissue, spring 34 is compressed such that cutting element 32 moves toward tissue, shown by arrow A, such that cutting element 32 cuts or pierces the tissue. As spring 34 is released, cutting element 32 moves back to its original position as shown by arrow B. Vacuum 46 is positioned within or outside of shaft 12 can be utilized to suction the cut nerve and/or soft tissue such that device 10 can be reinserted for additional cutting.

In another embodiment, the cutting device defines a small channel configured for injection of irrigation fluid to the surgical site to wash out the surgical site. The irrigation fluid may also facilitate suction of loose tissue fragments, and/or to cool ablated tissue.

In one embodiment, shaft 12 is operatively coupled to a source of navigational capability to allow easier pushing through the tissues. In various embodiments, the methods of cutting disclosed herein can include a pre-procedure step wherein the probe or needle can be coupled to a CT, MRI, PET machine, or the like so that the target nerve and/or soft tissue to be cut can be identified and accurately located during the resection procedure.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of cutting tissue of a patient comprising:
    inserting a cannula to form a hole in the tissue;
    inserting a cutting device through the cannula, the cutting device comprising:
        an elongated shaft having a proximal end and a distal end, the elongated shaft defining a longitudinal axis, the elongated shaft including a lower portion extending from the distal end toward the proximal end of the elongated shaft, the lower portion including an outer surface and an inner surface, the inner surface being spaced apart from the outer surface, and including a first portion extending from the distal end toward the proximal end in a first path to a first junction, a second portion extending from the first junction toward the outer surface in a second path to a second junction, and a third portion extending from the second junction toward the proximal end in a third path, wherein the outer surface of the lower portion, and the inner surface of the lower portion are connected together proximal the distal end to define a blunt end, the blunt end being configured to contact tissue adjacent the tissue to be cut;
        an upper portion extending from the distal end of the elongated shaft toward the proximal end of the elongated shaft, the upper portion including an outer surface and an inner surface, the inner surface being spaced apart from the outer surface and including a first portion extending from the distal end toward the proximal end in a first path to a first junction, a second portion extending from the first junction toward the outer surface in a second path to a second junction, and a third portion extending from the second junction toward the proximal end, a length of the lower portion between the proximal end and the distal end being greater than a length of the upper portion between the proximal end and the distal end; and
        a cutting element disposed between the lower portion and the upper portion and configured for retractable extension beyond the distal end of the elongated shaft so as to contact the tissue to be cut, the cutting element configured to cut at least a portion of the tissue to be cut, thereby producing cut tissue; and
        sliding the blunt end along a lamina of the patient to prevent damage to tissue;
    extending the cutting element beyond the upper and lower portions to cut tissue;
    retracting the cutting element into the cutting device; and
    removing the cutting device and the cannula.

2. The method of cutting tissue as recited in claim 1, wherein the inner surface of the lower portion and the inner surface of the upper portion form a cavity configured to house the cutting element.

3. The method of cutting tissue as recited in claim 1, wherein the cutting element is resiliently biased such that a cutting portion extends out of the cavity so as to contact and cut the tissue to be cut.

4. The method of cutting tissue as recited in claim 1, wherein the cutting element is spring loaded such that a cutting portion extends out of the cavity so as to contact and cut the tissue to be cut.

5. The method of cutting tissue as recited in claim 1, wherein the cutting element comprises a cutting tip configured to pierce the tissue to be cut.

6. The method of cutting tissue as recited in claim 1, wherein the cutting element includes at least one electrode, the at least one electrode configured to emit RF energy, the RF energy adapted to cut the tissue to be cut.

7. The method of cutting tissue as recited in claim 6, further comprising an electrically insulated layer adjacent to and exposing the cutting element such that the RF energy is centralized at the cutting element.

8. The method of cutting tissue as recited in claim 1, wherein the cutting element is further configured to emit plasma energy for destruction of the tissue to be cut.

9. The method of cutting tissue as recited in claim 1, wherein the elongated shaft further includes an attachment to a vacuum to produce suction so as to remove the cut tissue.

10. The method of cutting tissue as recited in claim 1, wherein the lower portion further includes a first thickness between the outer surface of the lower portion and the first portion of the lower portion, the first thickness of the lower portion being defined proximate the proximal end and extending perpendicular to the longitudinal axis, and a second thickness between the outer surface of the lower portion and the third portion of the lower portion, the second thickness of the lower portion being defined intermediate the distal end and the proximal end and extending perpendicular to the longitudinal axis, the first thickness of the lower portion being greater than the second thickness of the lower portion.

11. The method of cutting tissue as recited in claim 1, wherein the first portion of the lower portion includes a length, the length of the first portion of the lower portion being less than at least one of the first thickness of the lower portion and the second thickness of the lower portion.

12. The method of cutting tissue as recited claim 1, wherein the first portion of the inner surface of the lower portion is parallel to the longitudinal axis.

13. The method of cutting tissue as recited in s claim 1, wherein the third portion of the inner surface of the lower portion is parallel to the longitudinal axis.

14. The method of cutting tissue as recited in claim 1, wherein the second path of the lower portion is at least partially arcuate.

15. The method of cutting tissue as recited in claim 1, wherein the upper portion further includes a first thickness between the outer surface of the upper portion and the first portion of the upper portion, the first thickness of the upper portion being defined proximate the distal end and extending perpendicular to the longitudinal axis, and a second thickness of the upper portion between the outer surface of the upper portion and the third portion of the upper portion, the second thickness of the upper portion being defined intermediate the distal end and the proximal end and extending perpendicular to the longitudinal axis, the first thickness of the upper portion being greater than the second thickness of the upper portion.

16. The method of cutting tissue as recited in claim 15, wherein the first portion of the upper portion includes a length, the length of the first portion of the upper portion being less than at least one of the first thickness of the upper portion and the second thickness of the upper portion.

17. The method of cutting tissue as recited in claim 1, wherein the first portion of the inner surface of the upper portion is parallel to the longitudinal axis.

18. A method of cutting tissue of a patient comprising:
inserting a cannula to form a hole in the tissue;
inserting a cutting device through the cannula, the cutting device comprising:
an elongated shaft having a proximal end and a distal end, the elongated shaft defining a longitudinal axis, the elongated shaft including a lower portion extending from the distal end toward the proximal end of the elongated shaft, the lower portion including an outer surface and an inner surface, the inner surface being spaced apart from the outer surface, and including a first portion extending from the distal end toward the proximal end in a first path to a first junction, a second portion extending from the first junction toward the outer surface in a second path to a second junction, and a third portion extending from the second junction toward the proximal end in a third path, wherein the outer surface of the lower portion and the inner surface of the lower portion are connected together proximal the distal end to define a blunt end, the blunt end being configured to contact tissue adjacent the tissue to be cut;
an upper portion extending from the distal end of the elongated shaft toward the proximal end of the elongated shaft, the upper portion including an outer surface and an inner surface, the inner surface being spaced apart from the outer surface and including a first portion extending from the distal end toward the proximal end in a first path to a first junction, a second portion extending from the first junction toward the outer surface in a second path to a second junction, and a third portion extending from the second junction toward the proximal end, a length of the lower portion between the proximal end and the distal end being greater than a length of the upper portion between the proximal end and the distal end; and
a cavity formed between the inner surface of the lower portion and the inner surface of the upper portion, the cavity being configured to house a cutting element;
the cutting element housed in the cavity between the lower portion and the upper portion and configured to be resiliently biased for retractable extension beyond the distal end of the elongated shaft so as to contact the tissue to be cut, the cutting element configured to cut at least a portion of the tissue to be cut, thereby producing cut tissue;
sliding the blunt end along a lamina of the patient to prevent damage to tissue;
extending the cutting element beyond the upper and lower portions to cut tissue;
retracting the cutting element into the cutting device; and
removing the cutting device and the cannula.

19. The method of cutting tissue as recited in claim 18, wherein the cutting element is spring loaded such that a cutting portion extends out of the cavity so as to contact and cut the tissue to be cut.

20. The method of cutting tissue as recited in claim 18, wherein the cutting element is further configured to one of emit RF energy and emit plasma energy to facilitate removal of tissue.

* * * * *

UNITED STATES PATENT AND TRADEMARK OFFICE
CERTIFICATE OF CORRECTION

PATENT NO. : 9,820,807 B2
APPLICATION NO. : 15/238347
DATED : November 21, 2017
INVENTOR(S) : Arthur et al.

It is certified that error appears in the above-identified patent and that said Letters Patent is hereby corrected as shown below:

In Column 7, Line 20, delete "cavity 24" and insert -- cavity 30 --, therefor.

In Column 9, Line 26, in Claim 12, delete "recited claim" and insert -- recited in claim --, therefor.

In Column 9, Line 29, in Claim 13, delete "recited in s claim" and insert -- recited in claim --, therefor.

Signed and Sealed this
Twenty-ninth Day of May, 2018

Andrei Iancu
*Director of the United States Patent and Trademark Office*